(12) United States Patent
Inouye et al.

(10) Patent No.: US 9,243,234 B2
(45) Date of Patent: Jan. 26, 2016

(54) SEQUENCE-SPECIFIC MRNA INTERFERASE AND USES THEREOF

(75) Inventors: Masayori Inouye, New Brunswick, NJ (US); Yoshihiro Yamaguchi, Somerset, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/236,947

(22) PCT Filed: Aug. 3, 2012

(86) PCT No.: PCT/US2012/049581
§ 371 (c)(1),
(2), (4) Date: Mar. 7, 2014

(87) PCT Pub. No.: WO2013/020078
PCT Pub. Date: Feb. 7, 2013

(65) Prior Publication Data
US 2014/0294801 A1 Oct. 2, 2014

Related U.S. Application Data

(60) Provisional application No. 61/515,049, filed on Aug. 4, 2011.

(51) Int. Cl.
*C12N 9/22* (2006.01)
*C12Q 1/68* (2006.01)
(52) U.S. Cl.
CPC .............. *C12N 9/22* (2013.01); *C12Q 1/6869* (2013.01)

(58) Field of Classification Search
None
See application file for complete search history.

(56) References Cited

U.S. PATENT DOCUMENTS

2008/0058275 A1   3/2008   Inouye et al.

OTHER PUBLICATIONS

Bolhuis et al., "The genome of the square archaeon Haloquadratum walsbyi : life at the limits of water activity", BMC Genomics, 2006, 7:169. doi:10.1186/1471-2164-7-169.*
Ovchinnikov et al., The primary structure of *Escherichia coli* RNA polymerase. Nucleotide sequence of the rpoB gene and amino-acid sequence of the beta-subunit. Eur J Biochem, Jun. 1, 1989, vol. 116, No. 3, pp. 621-629.
UNIPROT. D2S2U4_HAL TV, Mar. 2, 2010 [online]. [Retrieved Oct. 3, 2012]. Retrieved from the internet: <URL: http://www.uniprot.org/uniprot/D2S2U4.txt?version=1>.
UNIPROT. F7P094_9EURY, Sep. 21, 2011[online].[Retrieved Oct. 3, 2012]. Retrieved from the internet: <URL: http://www.uniprot.org/uniprot/F7PQ94.txt?version=1>.
Yamaguchi et al., mRNA interferases, sequence-specific endoribonucleases from the toxin-antitoxin systems. Prog Mol Biol Transl Sci, 2009, vol. 85, pp. 467-500.

* cited by examiner

*Primary Examiner* — Suzanne M Noakes
(74) *Attorney, Agent, or Firm* — Fox Rothschild LLP

(57) ABSTRACT

The present invention provides an improved and specific mRNA interferase and related methods of protein-based mRNA interference.

7 Claims, 3 Drawing Sheets

SEQUENCE-SPECIFIC MRNA INTERFERASE AND USES THEREOF

CROSS REFERENCE TO RELATED APPLICATION

This application claims priority of U.S. Provisional Application No. 61/515,049, filed on Aug. 4, 2011. The content of the application is incorporated herein by reference in its entirety.

STATEMENT REGARDING FEDERALLY FUNDED RESEARCH

This invention was made with government support under grant 1RO1GM081567, awarded by the National Institute of Health. Accordingly, the U.S. Government has certain rights in this invention.

FIELD OF THE INVENTION

The present invention relates to a novel sequence-specific interferase and an improved method of achieving protein-based mRNA interference comparable to RNA-based mRNA interference, which is more sequence-specific.

BACKGROUND OF THE INVENTION

RNA-based mRNA interference has been well documented including the initial finding of natural antisense RNA regulation in *E. coli* and its application to regulate specific gene expression and phage infection and later the discovery of miRNA and siRNA. A common mechanism for all these systems is use of an RNA sequence complementary to a target mRNA. However, despite the existing technologies surrounding RNA-based mRNA interference, there are no functional technologies to inhibit the function of a specific mRNA by protein-based mRNA interference.

SUMMARY OF THE INVENTION

The present invention provides a novel mRNA interferase, which can mediate protein-based mRNA interference. Shown below are the polypeptide and related DNA sequences for an exemplary novel mRNA interferase, MazF-hw.

```
                                              (SEQ ID NO: 1)
VTPRCRYVQVRRGDIVIVDLSPTKGSEQQGTNRPCVVIQNDVGNRNSPT

TIIAPFTKQYNPDNTYPFEVEVLASNTSLNQDSVADLSQIRVVDINKGV

KTNIGSVPSARMAKIDTAIKTSLGL (SEQ ID NO: 2)
CATATGACTCCGCGTTGTCGTTACGTGCAAGTACGCCGCGGCGATATCG

TCATTGTTGACTTGAGTCCGACGAAGGGTAGCGAGCAGCAGGGTACCAA

CCGCCCTTGTGTAGTTATCCAAAATGATGTGGGCAACCGTAACTCCCCG

ACCACGATCATCGCTCCGTTCACGAAGCAGTATAACCCGGATAATACGT

ACCCGTTCGAAGTAGAGGTACTGGCATCGAATACCTCGCTGAATCAGGA

TTCGGTGGCAGACCTGAGTCAAATCCGCGTAGTGGATATTAATAAGGGC

GTGAAGACCAATATCGGCTCAGTTCCTTCCGCTCGCATGGCAAAAATCG

ATACCGCGATTAAGACGAGTCTGGGTCTGTGA
```

Accordingly, one aspect of this invention provides an isolated polypeptide (i) comprising an amino acid sequence that is at least 70% (e.g., 80, 85, 90, 95, or 99%) identical to the sequence of SEQ ID NO: 1 and (ii) having an mRNA interferase activity. In one embodiment, the polypeptide comprises, consists essentially of, or consists of the sequence of SEQ ID NO: 1 as shown below. In a preferred example, the polypeptide has an activity of cleaving an RNA sequence having the target sequence of UUACUCA (SEQ ID NO: 3).

Another aspect of this invention provides an isolated nucleic acid comprising a sequence that encodes the above-mentioned polypeptide. The nucleic acid can contain a sequence that is at least 70% (e.g., 80, 85, 90, 95, or 99%) identical to SEQ ID NO: 2. The invention also features a vector, such as an expression vector, comprising the nucleic acid and a host cell comprising the nucleic acid.

The afore-mentioned nucleic acid, vector, and host cell can be used for producing a polypeptide of this invention. Accordingly, this invention also provides a method for producing the polypeptide. The method includes culturing the host cell in a medium under conditions permitting expression of a polypeptide encoded by the nucleic acid, and purifying the polypeptide from the cultured cell in the medium of the cell.

In a third aspect, the invention provides a composition containing the aforementioned polypeptide or a nucleic acid encoding the polypeptide; and a carrier. As disclosed herein, this composition is useful for protein-based mRNA interference.

In a fourth aspect, the invention provides a method for detecting whether RNA molecules in a test sample have the target sequence of UUACUCA. The method includes incubating the test sample with the aforementioned polypeptide under conditions permitting cleaving an RNA sequence by the polypeptide to generated a treated sample; and examining the treated sample to identify any change in molecular weight or size of the RNA molecules. The change indicates that the RNA molecules have the target sequence. In one embodiment, the examining step is conducted by comparing the treated sample with a molecular weight maker sample or with a control sample that is identical to the test sample.

In a fifth aspect, the invention provides a method for decreasing the level of RNA in a cell. The method includes introducing to the cell the above-mentioned polypeptide, nucleic acid, or vector. In one example, the RNA contains the sequence of UUACUCA. The cell can be a prokaryotic cell (e.g., a bacterial cell such as an *E. coli*, cell) or a eukaryotic cell (e.g., a yeast cell, a plant cell, an insect cell, or a mammalian cell).

In a sixth aspect, the invention provides an isolated nucleic acid comprising (i) a sequence encoding a biological active agent and (ii) a restrictive sequence encoding UUACUCA. This nucleic acid allows one to generate various constructs where the expression level of the agent in a cell can be regulated by the polypeptide of this invention.

In a seventh aspect, the invention provides a kit comprising the polypeptide mentioned above and a buffer. The kit allows one to detect whether RNA molecules in a test sample have a specific target sequence, such as UUACUCA, or to protein-based mRNA interference.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1a-c show the characteristics of the MazF homologue from *H. walsbyi*. a, Amino acid sequence alignment of *H.* walsbyi MazF-hw (SEQ ID NO: 1) with 17 other MazF homologues (SEQ ID NOs: 7-23) from *B. subtilis* 168 (MazF-bs), *C. perfigens* 13 (MazF-cp), *S. Aureus* COL (MazF-sa), Nostoc PCC7120 (MazF-no), Synechocystis PCC6803 (MazF-sy), *M. tuberculosis* H37Rv (MazF-mt1 to -mt7), ChpBK in *E. coli* (ChpBK-ec), PemK in *E. coli* (PemK-ec), *M. xanthus* (MazF-mx) and MazF from *E. coli* K12 (MazF-ec). Identical amino acid residues are shown in black shades and conservative substitutions in gray shades. S represents β sheet strands and H represents α helices. b, Location of the mazF-hw gene on the *H. walsbyi* chromosome obtained from TIGR. c, Toxicity of *H. walsbyi* MazF-hw. *E. coli* BL21 cells were transformed with pColdIIImazF-hw and spread on M9-glycerol-casamino acids plates with and without IPTG (1 mM). The plates were incubated at 37° C. for 18 h. d, Effect of MazF-hw induction on cell growth. Cell growth was measured by a Klett meter. *E. coli* BL21 cells harboring pColdIII-mazF-hw were cultured in M9-glycerol-casamino acids medium at 37° C. until cell density reached 30 Klett (equivalent to $3 \times 10^7$ cells/ml). Then, the culture was divided into two; one was incubated at 37° C. with (open circles) and the other without IPTG (1 mM; closed circles). The cultures were diluted 10 fold at 2 h and 5 h time points, respectively.

Figures 1A, 1B, 1C, 1D:
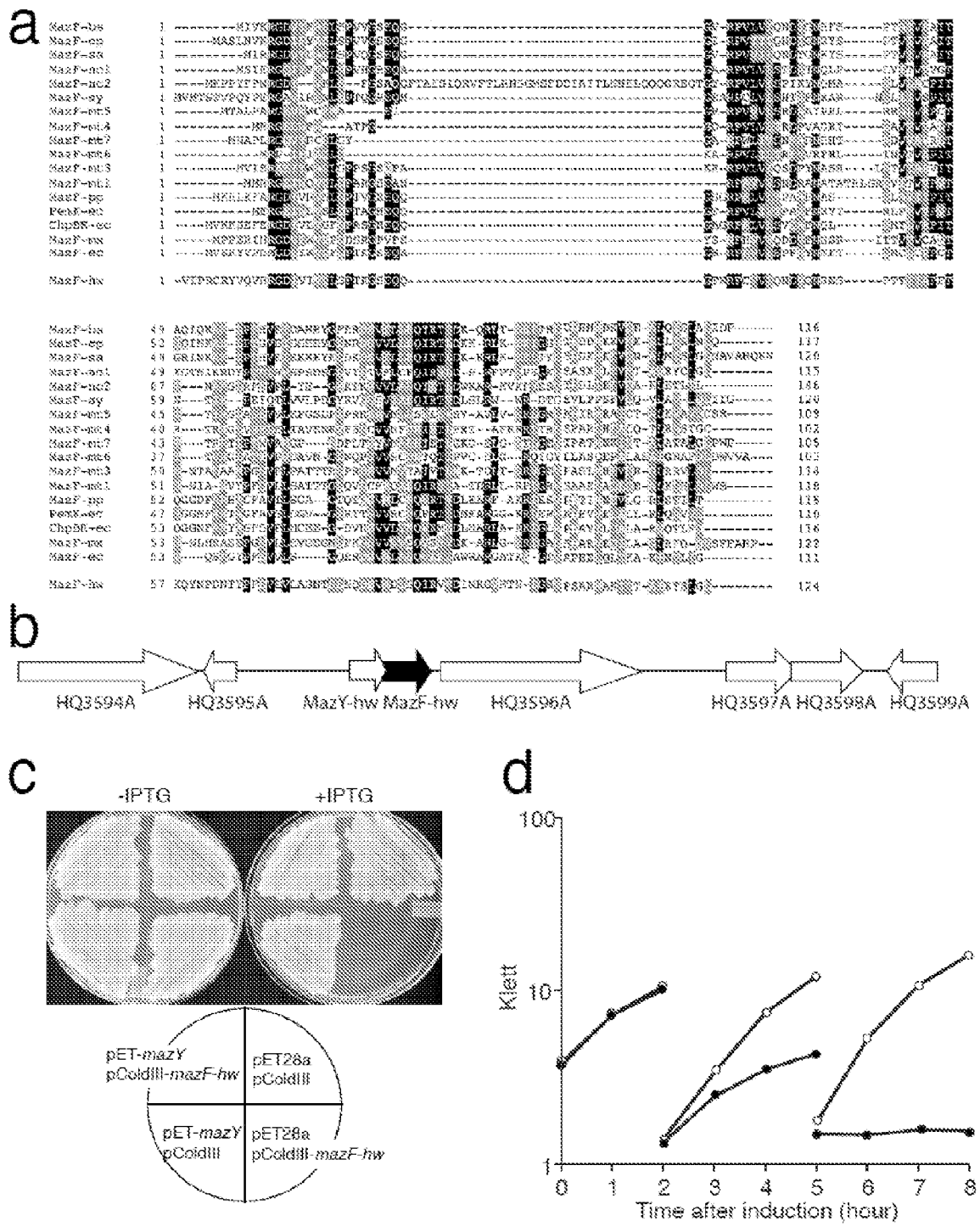

FIGS. 2a-f show the endoribonuclease activity of MazF-hw in vitro. Cleavage of MS2phage RNA (a), *E. coli* total RNA (b), and yeast total RNA (c) by MazF-hw. Purified MazF-hw was incubated with *E. coli* total RNA, yeast total RNA and MS2 phage RNA at 37° C. for 30 min with or without purified CspA protein (lanes 2 and 3). The reaction mixture (20 μl) consisted of each RNA, 0.5 μg MazF-hw, 120 μg CspA, 0.1 M EDTA, 40 mM NaCl and 0.5 μl of RNase inhibitor (Roche) in 20 mM Tris-HC1 (pH8.0)12. The reaction products were analyzed on a 1.2% agarose gel. The products are indicated by arrows. d, Analysis of MazF-hw cleavage sites in MS2 phage RNA by in vitro primer extension. Lane 1 represents a control reaction in which no protein was added; lane 2, MS2 RNA was incubated with MazF-hw. The reactions were analyzed on a 6% polyacrylamide gel containing 8 M urea and the products were visualized by autoradiography. The cleavage site is indicated by an arrow on the RNA sequence (SEQ ID NO: 6) and determined using the RNA ladder shown on the left. e and f, Synthesized 13-base RNA (5'-A1A2G3U4U5A6C7U8 C9A10A11A12G13-3', SEQ ID NO: 3) in which the U4 and A10 residues were replaced with A, G, and C or with G, C, and U residues, respectively, used as substrates. The substrates labeled at the 5'-end with 32P were incubated with MazF-hw for 0, 5 and 30 min (lanes 1-3, respectively) or without MazF-hw for 30 min (lane 4). The reaction products were analyzed on a 20% polyacrylamide gel containing 8 M urea and the products were visualized by autoradiography.

FIGS. 3a-e demonstrate that four essential genes containing hepta-sequence are essential for MazF-hw toxicity. Total RNA was extracted from *E. coli* BL21(DE3) cells harboring pColdII mazF-hw (a) and pColdII (b) at various time points (0, 5, 10, 30 and 60 min) after the addition of 0.1 mM IPTG and subjected to reverse transcriptase PCR (RT-PCR). RT-PCR was performed using the protocol for the Transcriptor first strand cDNA synthesis kit (Roche) and the primers for four genes were designed to amplify the fragment containing hepta-sequence cutting site. e, The four UUACUCA-less genes were cloned into pACYC-Duet and pCOLA-Duet. *E. coli* BL21 (DE3) cells harboring these plasmids and pColdII-mazF-hw were streaked on M9 plates with or without 0.1 mM IPTG and incubated at 30° C. for 20 h.

DETAILED DESCRIPTION OF INVENTION

RNA-based mRNA interference by antisense RNA and RNAi has been well documented and used to suppress a specific gene expression. More recently, protein-based mRNA interference by sequence-specific endoribonulceases (i.e., mRNA interferases) has been implicated by earlier findings of three or five-base sequence-specific mRNA interferases in bacteria. However, these enzymes were not specific enough to regulate expression of a specific gene(s) in the cells. To achieve protein-based mRNA interference comparable to RNA-based mRNA interference, more sequence-specific mRNA interferases are required.

As disclosed herein, an mRNA interferase was identified from an extreme halophilic archaeon, which recognizes a specific seven-base sequence cleaving only a specific group of genes required for ATP production. This archaeon, *Haloquadra walsbyi,* isolated from a hypersaline pool on the Sinai Peninsula contains a gene encoding a protein (MazF-hw) homologous to *Escherichia coli* MazF-ec, an ACA-specific mRNA interferase. The induction of MazF-hw in *E. coli* resulted in complete cell growth arrest only after three generations in contrast to MazF-ec causing almost immediate growth arrest. Purified MazF-hw cleaved only at a single site in 3.5-kb MS2 phage RNA, but could not cleave *E. coli* 16S and 23S rRNAs or yeast 18S and 28S rRNAs. Determination of the cleavage site in MS2 RNA and assays with synthetic oligoribonucleotides revealed that MazF-hw cleaves RNA specifically at UU^ACUCA, (cleaved at ^). This sequence was found to be unusually abundant in the mRNAs for rhodopsin transcription activator and some membrane proteins of the archaeon. *E. coli* contains four essential genes having the hepta sequence. When all the cleavage sites in these genes were eliminated, *E. coli* was no longer sensitive to MazF-hw, demonstrating that cell growth can be regulated by a sequence-specific mRNA interferase. These findings suggest that, in addition to antisense RNA, protein-based mRNA interference is another effective way to silence specific gene expression in cells.

The present invention provides an enzyme isolated from a super halophilic archaeon isolated from a hypersaline pool on the Sinai Peninsula, which functions as an endoribonuclease or an mRNA interferase, termed MazF-hw. It recognizes a specific 7-base RNA sequence. Theoretically, a specific 7-base sequence exists once in every 16,384-base sequence, but interestingly the hepta RNA sequence is overrepresented in the rhodopsin transcription activator gene and a few membrane protein genes of this archaeon, indicating that protein-based mRNA interference occurs in this organism to silence specific gene expression and regulate cell growth. When MazF-hw is induced in *E. coli,* cell growth is arrested after three generations, indicating that there are a few essential genes containing the hepta sequence. In fact, four essential genes on the *E. coli* genome were found to contain one hepta sequence each. To verify if protein-based mRNA interference can regulate cell growth, all four hepta sequences were altered to uncleavable sequences without changing the amino acid sequences. It was found that when these hepta sequence-less genes are induced, the cells become resistant to MazF-hw induction. Thus, this is the first demonstration that cell growth can be regulated by protein-based mRNA interference targeting specific genes. This result further demonstrates that protein-based mRNA interference by sequence-specific mRNA interferases may be widely applicable for regulation of specific gene expression and thus cell growth from bacteria to human.

As used herein, the percent identity of two amino acid sequences or of two nucleic acids is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic. Acids Res.* 25(17):3389-3402, 1997. When utilizing BLAST and Gapped BLAST programs, the default parameters of the respective programs (e.g., XBLAST and NBLAST) can be used.

An "isolated polypeptide" refers to a polypeptide that has been separated from other proteins, lipids, and nucleic acids with which it is naturally associated. The polypeptide can constitute at least 10% (i.e., any percentage between 10% and 100% inclusive, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods.

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide, polypeptide, or protein refers to a peptide, polypeptide, or protein prepared by chemical synthesis. The term "recombinant" when used with reference e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

Within the scope of this invention are fusion proteins containing one or more of the afore-mentioned sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

The amino acid composition of the above-mentioned mRNA interferase peptide/polypeptide/protein may vary without disrupting the ability to recognize a specific RNA sequence and cleaved it. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in SEQ ID NO: 1 is preferably replaced with another amino acid residue from the same side chain family. Alternatively, mutations can be introduced randomly along all or part of the sequences, such as by saturation mutagenesis, and the resultant mutants can be screened for the ability to bind to the respective receptor and trigger the respective cellular response to identify mutants that retain the activity as descried below in the examples.

A functional equivalent of a peptide, polypeptide, or protein of this invention refers to a polypeptide derivative of the peptide, polypeptide, or protein, e.g., a protein having ore or more point mutations, insertions, deletions, truncations, a fusion protein, or a combination thereof. It retains substantially the activity to of the above-mentioned mRNA interferase. The isolated polypeptide can contain SEQ ID NO: 1 or a functional fragment thereof. In general, the functional equivalent is at least 70% (e.g., any number between 70% and 100%, inclusive, e.g., 70%, 80%, 85%, 90%, 95%, and 99%) identical to SEQ ID NO: 1.

A polypeptide described in this invention can be obtained as a recombinant polypeptide. To prepare a recombinant polypeptide, a nucleic acid encoding it can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Alternatively, the peptides/polypeptides/proteins of the invention can be chemically synthesized (see e.g., Creighton, "Proteins: Structures and Molecular Principles," W. H. Freeman & Co. NY, 1983), or produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

As an mRNA interferase functions intracellularly, the above-disclosed polypeptide can be associated with, e.g., conjugated or fused to, one or more of an amino acid sequence comprising a cell-penetrating peptide (CPP) sequence and the like. In this manner, as composition of the invention as discussed below can include a transport enhancer. For example, the composition may include a penetration enhancing agent, such as MSM, for the delivery of the mRNA interferase or related gene-silencing polypeptides to a cell and/or through the cell membrane and into the cytosol or nucleus of the cell. The mRNA interferase or related therapeutic polypeptides then function to down-regulate the mRNA level of a target gene, thereby resulting in a desired cell status and phenotype. As indicated above, the mRNA interferase or related gene-silencing polypeptides may be delivered by itself or as a fusion with one or more of an NLS, CPP, and/or other domains. See, e.g., Tachikawa et al. PNAS (2004) vol. 101, no. 42:15225-15230.

A cell-penetrating peptide (CPP) generally consists of less than 30 amino acids and has a net positive charge. CPPs internalize in living animal cells in vitro and in vivo in endocytotic or receptor/energy-independent manner. There are several classes of CPPs with various origins, from totally protein-derived CPPs via chimeric CPPs to completely synthetic CPPs. Examples of CPPs are known in the art. See, e.g., U.S. Application Nos. 20090099066 and 20100279918. It is know that CPPs can delivery an exogenous protein to a specific cell.

Although the mRNA interferase or related gene-silencing polypeptides to be delivered may be fusion proteins including a CPP, in certain instances, the interferase does not include a CPP as the aforementioned transport enhancer may serve the function of delivering the biologically active interferase directly to the cell, and/or through the cell membrane into the cytoplasm of the cell and/or into the nucleus of the cell as desired. For instance, in certain instances, it may be desirable to deliver a biologically active protein to the cell wherein the protein is not conjugated or fused to another molecule. In such an instance, any biologically active protein may be delivered directly in conjunction with the transport enhancer.

All of naturally occurring mRNA interferase, genetic engineered mRNA interferase, and chemically synthesized mRNA interferase can be used to practice the invention disclosed therein. mRNA interferase polypeptides obtained by recombinant DNA technology may have the same amino acid sequence as naturally a occurring mRNA interferase or an functionally equivalent thereof. They also include chemically modified versions. Examples of chemically modified polypeptides include polypeptides subjected to conformational change, addition or deletion of a side chain, and polypeptides to which a compound such as polyethylene glycol has been bound. Once purified and tested by standard methods or according to the method described in the examples below, an mRNA interferase polypeptide can be included in pharmaceutical composition for silencing a gene.

The present invention also provides a nucleic acid that encodes any of the polypeptides mentioned above. Preferably, the nucleotide sequences are isolated and/or purified. A nucleic acid refers to a DNA molecule (for example, but not limited to, a cDNA or genomic DNA), an RNA molecule (for example, but not limited to, an mRNA), or a DNA or RNA analog. A DNA or RNA analog can be synthesized from nucleotide analogs. The nucleic acid molecule can be single-stranded or double-stranded. An "isolated nucleic acid" is at nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The present invention also provides recombinant constructs or vectors having one or more of the nucleotide sequences described herein. Example of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like.

Examples of expression vectors include chromosomal, nonchromosomal and synthetic DNA sequences, e.g., derivatives of or Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, as nucleic acid sequence encoding one of the polypeptides described above can be inserted into an appropriate restriction endonuclease site(s) by procedures known in the art. Such procedures and related sub-cloning procedures are within the scope of those skilled in the art.

The nucleic acid sequence in the aforementioned expression vector is preferably operatively linked to an appropriate transcription control sequence (promoter) to direct mRNA synthesis. Examples of such promoters include: the retroviral long terminal (LTR) or SV40 promoter, the *E. coli* lac or tip promoter, the phage lambda PL promoter, and other promoters known to control expression of genes in prokaryotic or eukaryotic cells or viruses. In a preferred embodiment, the promoter is a tissue specific promoter that drives mRNA synthesis in a cell or tissue of interest.

The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli*.

The vector containing the appropriate nucleic acid sequences as described above, as well as an appropriate promoter or control sequence, can be employed to transform an appropriate host to permit the host to express the polypeptides described above (e.g., SEQ ID NO: 1). Such vectors can be used in gene therapy. Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEX 293), adenoviruses, and plant cells. The selection of an appropriate host is within the scope of those skilled in the art. In some embodiments, the present invention provides methods for producing the above mentioned polypeptides by transfecting a host cell with an expression vector having a nucleotide sequence that encodes one of the polypeptides. The host cells are then cultured under a suitable condition, which allows for the expression of the polypeptide.

The present invention further provides gene therapy using nucleic acids encoding one or more of the polypeptides mentioned above or an analog or homolog thereof. Targeted gene therapy involves the use of vectors (e.g., organ-homing peptide) that are targeted to specific organs or tissues after systemic administration.

In certain embodiments, the present invention provides gene therapy for the in vivo production of the above-mentioned polypeptides. Such therapy would achieve its therapeutic effect by introduction of the nucleic acid sequences into cells or tissues of a human or a non-human animal in need of deceasing in or silencing of a target gene. Delivery of the nucleic acid sequences can be achieved using a recombinant expression vector such as a chimeric virus or a colloidal dispersion system. Preferred for therapeutic delivery of the nucleic acid sequences is the use of targeted liposomes.

Various viral vectors which can be utilized for gene therapy disclosed herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney marine leukemia virus (MoMuLV), Harvey marine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using a tissues- or cell-specific antibody or hormone that has a receptor in a cell. Those of skill in the art will recognize that specific polynucleotide sequences can be inserted into the retroviral genome or attached to a viral envelope to allow target specific delivery of the retroviral vector.

Another targeted system for delivery of nucleic acids is a colloidal dispersion system. Colloidal dispersion systems include macromolecule complexes, nanocapsules, microspheres, beads, and lipid-based system including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA, and intact virions can be encapsulated within the aqueous interior and be delivered to cells in a biologically active form. Methods for efficient gene transfer using a liposome vehicle, are known in the art. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Exemplary phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art. A nucleic acid sequence of this invention can be a DNA or a RNA. The terms "RNA," "RNA molecule," and "ribonucleic acid molecule" are used interchangeably herein, and refer to a polymer of ribonucleotides. The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA also can be chemically synthesized. DNA and RNA can be single-stranded (i.e., ssRNA and ssDNA, respectively) or multi-stranded (e.g., double-stranded, i.e., dsRNA and dsDNA, respectively).

Compositions

This invention also provides a composition that contains a suitable carrier and one or more of the agents described above. The composition can be a pharmaceutical composition that contains a pharmaceutically acceptable carrier. The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

The above-described composition, in any of the forms described above, can be used for modulating the mRNA level of a gene. An effective amount refers to the amount of an active compound/agent that is required to confer a therapeutic effect on a treated subject. Effective doses will vary, as recognized by those skilled in the art, depending on the types of conditions treated, route of administration, excipient usage, and the possibility of co-usage with other therapeutic treatment.

A pharmaceutical composition of this invention can be administered to a subject parenterally, orally, nasally, rectally, topically, or buccally. The term "parenteral" as used herein refers to, but not limited to, subcutaneous, intracutaneous, intravenous, intramuscular, intraarticular, or intraarterial injection, as well as any suitable infusion technique. A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, TWEENS or SPANS or other similar emulsifying agents or bioavailability enhancers, which are commonly used in the manufacture of pharmaceutically acceptable solid, liquid, or other dosage forms also can be used for the purpose of formulation. As used herein, "administering" does not include microinjection of a fertilized oocyte and intergenerational transmission via germ cells.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model. "Treating" or "treatment" refers to administration of a compound or agent to a subject who has a disorder with the purpose to cure, alleviate, relieve, remedy, delay the onset of, prevent, or ameliorate the disorder, the symptom of the disorder, the disease state secondary to the disorder, or the predisposition toward the disorder. An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

Kits

The invention provides a kit for determining whether RNA molecules in a test sample have a specific target sequence, such as UUACUCA, or for protein-based mRNA interference. To that end, a wide variety of kits may be prepared according to present invention. For example, a kit may include the above-motioned polypeptide, buffers, and instructional materials for RNA restriction enzymatic reaction. While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

The kits of the present invention may further include one or more of the following components or reagents: a reverse transcriptase, an RNase inhibitor, an enzyme for attaching a 3' oligodeoxynucleotide tail onto DNA molecules (e.g., terminal deoxynucleotidyl transferase), an enzyme for degrading RNA in RNA/DNA duplexes (e.g., RNase H); and one or more RNA polymerases (e.g., T7, T3 or SP6 RNA polymerase). Additionally, the kits may include buffers, primers (e.g., oligodT primers, random primers), nucleotides, labeled nucleotides, an RNase inhibitor, polyA polymerase, RNase-free water, containers, vials, reaction tubes, and the like compatible with the analysis of RNA molecules according to the methods of the present invention. The components and reagents may be provided in containers with suitable storage media.

EXAMPLE 1

Materials and Methods

This example describes general materials and methods used in EXAMPLES 2-4 below.

Bacterial Strains and Plasmids

E. coli BL21(DE3) and DH5a were used. The mazF-hw gene was synthesized (Genscript) and cloned into pColdII (Takara Bio) to express the MazFhw. The four UUACUCA-less genes (rpoB, lolD, rplC and rpmD) were cloned into pACYCDuet and pCOLA-Duet (Novagen), respectively.

Poem Purification

To purify N-terminal His-tagged MazF-hw, pColdII-mazF-hw was introduced into E. coli BL21(DE3). The expression of MazF-hw was induced with 1 mM isopropyl-β-D-1-thiogalactoside (IPTG) at 15° C. for 3 h. The MazF-hw was purified with Ni-NTA agarose (Qiagen) following the manufacturer's protocol.

mRNA Interferase Activity of MazF-hw

Purified MazF-hw was incubated with E. coli total RNA, yeast total RNA and MS2 phage RNA at 37° C. for 30 min with or without purified CspA protein, an RNA chaperone. The reaction mixture (20 μl) consisted of each RNA, 0.5 μg MazF-hw, 120 μg CspA, 0.1 mM EDTA, 400 mM NaCl and 0.5 μl of RNase inhibitor (Roche) in 20 mM Tris-HCl (pH8.0). After denaturation in urea, the products were separated on an 1.2% agarose gel.

Primer Extension Analysis in Vitro

MS2 RNA was incubated with or without purified MazF-hw as described above and the products were analyzed as described previously.

Cleavage of Synthetic RNA by MazF-hw

Synthesized 13-base RNA (5'-$A_1A_2G_3U_4U_5A_6C_7U_8C_9A_{10}A_{11}A_{12}G_{13}$-3') (SEQ ID NO.: 3) in which the U4 and A10 residues were replaced with A, G, and C or G, C, and U residues, respectively, were used as substrate. The labeled substrates were incubated with MazF-hw for 0, 5 and 30 min or without MazF-hw for 30 min at 20° C. in a reaction mixture containing 20 mM Tris-HCl (pH8.0), 1 mM EDTA, 400 mM NaCl and 0.5 μl of RNase inhibitor. The reaction products were analyzed as described previously

EXAMPLE 2

Identification of a MazF Homologue in H. Walsbyi

In this example, assays were carried out to identify a MazF homologue Haloquadra walsbyi.

Haloquadra walsbyi was isolated from a hypersaline pool on Sinai Peninsula. The cells were extremely thin and square, measuring 2-5 μm wide but less than 0.2 μm thick. Using blast search with E. coli MazF, the gene HQ2202A was identified. It encodes a 124-residue protein. This protein has 31% identity and 46% similarity to E. coli MazF (111 residues) (FIG. 1a). The gene for MazF-hw appears to be co-translated with the gene for an upstream ORF, which overlaps with MazF ORF in a manner similar to that of the E. coli mazE-mazF operon (FIG. 1b). However the upstream ORF (termed MazY) does not show homology to E. coli MazE, the antitoxin of MazF.

In order to examine MazF-hw toxicity in E. coli, the mazF-hw gene was synthesized and cloned into pColdII vector. As shown in FIG. 1c, the induction of MazF-hw inhibited colony formation on an agar plate in the presence of 1 mM isopropyl-β-D-1-thiogalactoside (IPTG). The gene for MazY-hw was also synthesized and cloned it into pET28a. As shown in FIG. 1c, co-induction of MazY-hw neutralized the toxicity of MazF-hw, suggesting that MazY is the antitoxin for MazF-hw. The toxicity of MazF-hw in was also examined a liquid culture (FIG. 1d). When MazF-hw was induced by the addition of 1 mM IPTG, cell growth was completely inhibited only after 5 hr or three generations. This slow growth inhibition is in a sharp contrast to that observed with E. coli MazF, which inhibits cell growth within 15 min after induction.

EXAMPLE 3

MazF-hw 1s an mRNA Interferase

It was possible that this slow inhibitory effect of MazF-hw was likely due to its RNA cleavage specificity. Therefore, in this example, MazF-hw protein was purified to determine its cleavage specificity.

Figures 2A, 2B, 2C, 2D, 2E, 2F:
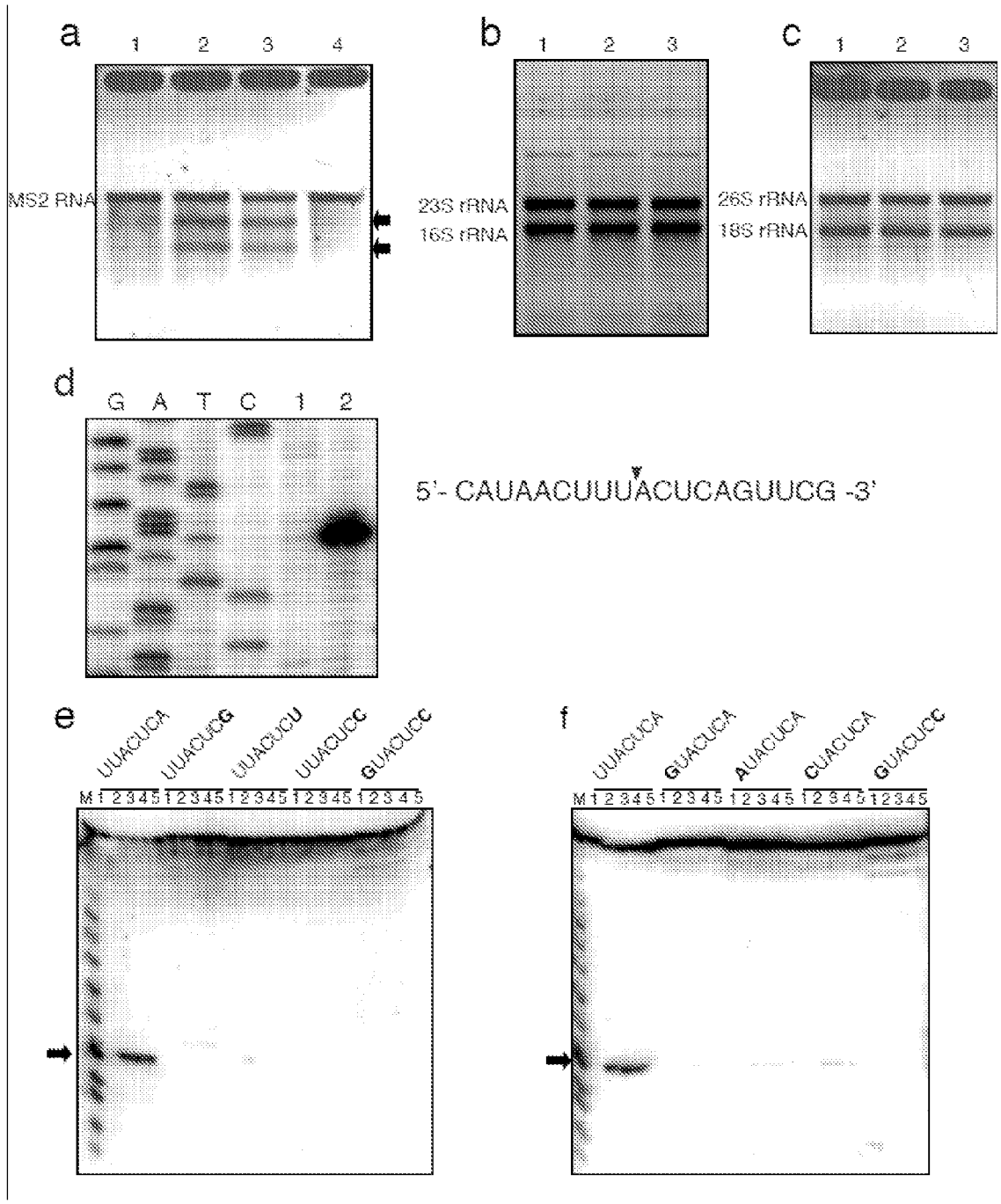

First, 3.5-kb MS2 phage RNA was used as substrate and found that MazF-hw cleaves this mRNA only at one site (FIG. 2a). It is important to note that preincubation of MazF-hw with MazY-hw completely inhibited its endoribonuclease activity, suggesting that the observed cleavage is caused by MazF-hw (FIG. 2a; lane 4). The specific cleavage site in MS2 RNA between—ACUUU and ACUCA—was detected by primer extension (FIG. 2d). The MazF-hw MS2 RNA cleavage activity was completely inhibited by addition of 10 mM $MgCl_2$ in the reaction as found with E. coli MazF8 and required NaCl (10-50 mM).

Next, assays were carried out using 16S and 23S rRNAs from E. coli and 18S and 28S rRNAs from yeast as substrate. Surprisingly, none of these RNAs were cleaved by MazF-hw (FIGS. 2b and e, respectively). Using Perl programming language for computational analysis, these RNAs were analyzed for the presence of different sequences (all possible four-, five- and six-base combinations) around the sequence of the sole cleavage site found in MS2 RNA. The results from these analyses are presented in Table 1 below and demonstrate that there are two possible six-base RNA cleavage sequences for MazF-hw, UUACUC and UACUCA, neither of which exists in E. coli 16S and 23S rRNAs or in yeast 18S and 28S rRNAs (the common bases in the sequences are underlined).

The results presented in FIG. 2 show that there is one cleavage site in MS2 RNA for MazF-hw and no cleavage sites in the E. coli 16S and 23S RNAs and the yeast 18S and 28S RNAs. Using Perl programming language for computational analysis, these RNAs were analyzed for the presence of all possible four-, five- and six-base combinations around the sequence of the sole cleavage site found in MS2 RNA. Results from these analyses are presented in Table 1.

TABLE 1

Putative MazF-hw cleavage sites in
MS2 RNA, 23S, 16S, 28S and 18S rRNA

|       | MS2RNA | 23S rRNA | 16S rRNA | 28S rRNA | 18S rRNA |
|-------|--------|----------|----------|----------|----------|
| CUUU  | >10    |          |          |          |          |
| UUUA  | >10    |          |          |          |          |
| UUAC  | >10    |          |          |          |          |
| UACU  | >10    |          |          |          |          |
| ACUC  | >10    |          |          |          |          |
| UUUAC | 9      | 1        | 0        | 2        | 2        |
| UUACU | 3      | 2        | 1        | 2        | 2        |
| UACUC | 1      | 3        | 0        | 1        | 0        |
| ACUCA | 2      | 1        | 2        | 1        | 2        |

TABLE 1-continued

Putative MazF-hw cleavage sites in
MS2 RNA, 23S, 16S, 28S and 18S rRNA

|        | MS2RNA | 23S rRNA | 16S rRNA | 28S rRNA | 18S rRNA |
|--------|--------|----------|----------|----------|----------|
| CUCAG  | 5      | 1        | 2        | 1        | 2        |
| UUUACU | 1      | 1        | 0        | 1        | 2        |
| UUACUC | 1      | 0        | 0        | 0        | 0        |
| UACUCA | 1      | 0        | 0        | 0        | 0        |
| ACUCAG | 1      | 1        | 0        | 0        | 0        |
| CUCAGU | 1      | 1        | 0        | 0        | 0        |

EXAMPLE 4

MazF-hw Cleaves RNA at a Specific Seven-Base Sequence

In order to determine which of the two sequences was the actual cleavage site, two 13-base oligonucleotides, 5'-AAG-UUACUCCAGG-3' (SEQ ID NO.: 4) and 5'-AAGCUACU-CAAGG-3' (SEQ ID NO.: 5) were synthesized The underlined sequences are from MS2 RNA including the common UACUC sequence. However, they were not cleaved by the MazF-hw (data not shown).

Subsequently, seven more 13-base oligoribonucleotides were synthesized. These oligoribonucleotides have various bases on both sides of the six-base sequences (FIGS. 2e and 2f). Surprisingly, it was found that MazF-hw cleaved only one of these substrates, containing UUACUCA sequence, which is consistent with the cleavage sequence found in MS2 RNA. Thus, the results demonstrate that MazF-hw recognizes the seven-base sequence, UU^ACUA and cleaves between the second (U) and the third residue (A)(^ indicates the cleavage site).

Since a specific seven-base sequence can be found on average only once every 16,384-base RNA sequence, it is possible that MazF-hw cleaves only a specific group of mRNAs. Out of 2610 ORFs on the H. walsbyi genome, only 183 ORFs have the heptad sequence, of which one has three heptad sequences, twelve have two (Table 2), and the remaining 170 have only one. Since one can assume that the mRNA sensitivity to MazF-hw is proportional to the number of the heptad cleavage sites present, the boa gene for a putative transcription activator for rhodopsin (bacterio-opsin) having three heptad sequences may be the most sensitive, suggesting that upon induction of MazF-hw the expression of the light-driven proton pump may be turned off.

TABLE 2

ORFs in *Haloquadra walsbyi*, which are most sensitive to MazF-hw

| Gene ID | Gene | Length (bp) | Number of UUACUCA | Protein Name | COGs | Halofex Function Class |
|---------|------|-------------|-------------------|--------------|------|------------------------|
| HQ1739A | boa  | 5418 | 3 | bacterio-opsin activator-like transcription regulator | COG2202T, COG2203T, COG3413R | SIG |
| HQ3529A | —    | 402  | 2 | probable sulfatase | COG3119P | MIS |
| HQ2658A | —    | 717  | 2 | conserved hypothetical protein | COG2220R | CHY |
| HQ2731A | glnP | 855  | 2 | ABC-type glutamine/glutamate/polar amino acids transport system, permease protein | COG0765E | TP |
| HQ2726A | trmB | 1062 | 2 | probable sugar-specific trancriptional regulator TrmB | COG1378K | REG |
| HQ1250A | gtl3 | 1065 | 2 | probable glycosyltransferase, type 2 | COG0463M | GEN |
| HQ3464A | aslA | 1605 | 2 | probable arylsulfatase; probable choline-sulfatase | COG3119P | MIS |
| HQ1036A | cstA | 1806 | 2 | carbon starvation protein A | COG1966T | SIG |

TABLE 2-continued

ORFs in *Haloquadra walsbyi*, which are most sensitive to MazF-hw

| Gene ID | Gene | Length (bp) | Number of UUACUCA | Protein Name | COGs | Halofex Function Class |
|---|---|---|---|---|---|---|
| HQ1786A | — | 1938 | 2 | ABC-type transport system ATP-binding/permease protein | COG1132V | TP |
| HQ2295A | chlID | 2289 | 2 | magnesium chelatase (protoporphyrin IX magnesium-chelatase) | COG1239H, COG1240H | COM |
| HQ2542A | | 2367 | 2 | conserved hypothetical protein | — | CHY |
| HQ2550A | glcD | 3111 | 2 | oxidoreductase (glycolate oxidase iron-sulfur subunit) | COG0247C, COG0277C | GEN |
| HQ3461A | polA2 | 6870 | 2 | DNA-directed DNA polymerase large subunit (family D) (archaeal DNA polymerase II) | COG1372L, COG1933L | RRR |

EXAMPLE 5

Regulation of Specific Gene By MazF-hw in *E. Coli*

In *E. coli*, out of 233 ORFs containing the heptad sequence, only four (lolD, rplC, rpmD and rpoB,) are essential for cell growth. Upon MazF-hw induction, mRNAs from all four of these genes were degraded (FIG. 3a), assays were carried out to test whether MazFhw was no longer toxic in *E. coli* if all the cleavage sites in the four genes were eliminated.

Figure 3A:
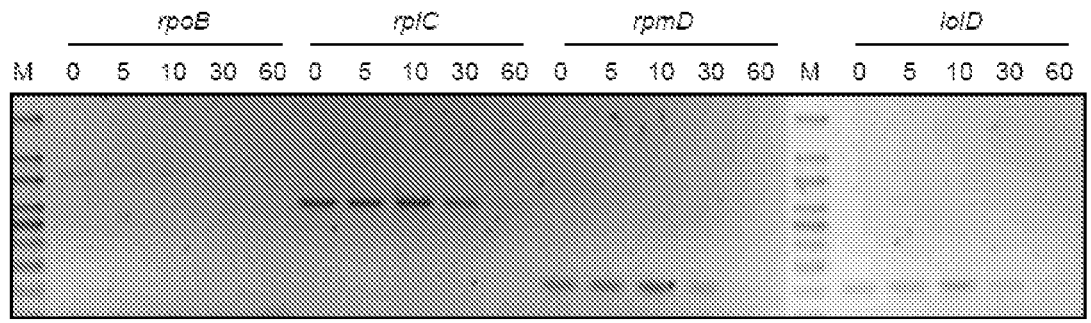
Figure 3B:
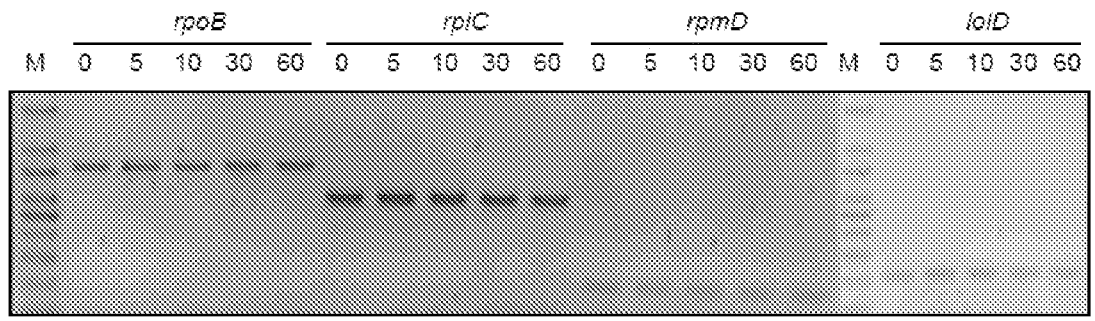
Figure 3C:
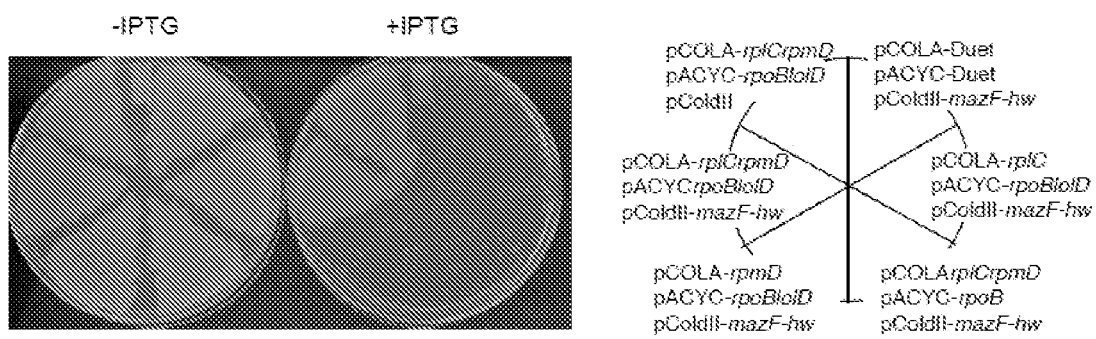

As shown in FIG. 3c, cell growth was recovered when the cleavage sites were removed from the four genes. Importantly, when one of the four genes was left intact, cell growth was blocked even in the presence of IPTG, demonstrating that cell growth can be regulated by a sequence-specific mRNA interferase. The data also confirmed that MazF-hw cleaves mRNA at UUACUCA sequences. Notably, the MazF-hw activity was strongly inhibited in the presence of 10 mM $MgCl_2$ or 500 mM NaCl, while *H. walsbyi* requires 3 M NaCl for cell growth and is resistant to 2 M $MgCl_2$ suggesting that MazF-hw is not active under normal growth conditions. This archaeon lives on the surface of saturated salt water, effectively utilizing light for the production of ATP. However, it is assumed that upon hypo-osmotic stress in nature such as rain or influx of water from a river lowering specific gravity of water, the cells cannot float on the surface of water, reducing ATP production. As a result, the cellular salt concentration decreases to activate MazF-hw, which then degrades the mRNA for transcription activator for the rhodopsin gene. Most of the genes containing two heptad sequences such as ABC-type transporters, cAMP-dependent carbon starvation protein A, sulfatase and FAD-linked oxidase (Table 2) also seem to be involved in hypo-osmotic stress.

While sequence-specific DNA restriction enzymes have been known for many years, sequence-specific endoribonucleases have just been recently discovered. To date, a number of MazF homologues are found in bacteria, having a wide range of cleavage specificities from three to five bases. It has been shown that pathogenic bacteria such as *Mycobacterium tuberculosis* and *Staphylococcus aureus* contain mRNA interferases that recognize specific pentad RNA sequences, which are either overpresented or underpresented in genes associated with their pathogenicity. In *Myxococcus xanthus*, a pentad sequence-specific mRNA interferase has been shown to be required for programmed cell death during fruiting body formation. The present discovery of a MazF homologue, specific to a heptad RNA sequence raises an intriguingly possibility that there may be many other MazF homologues which target only a specific group of cellular mRNAs to regulate cellular physiology. Notably, in addition of antisense RNA and siRNA technology, mRNA interferases will open a new avenue to interfere with expression of a specific mRNA or a specific group of mRNAs, preventing viral infection and harmful gene expression from bacteria to human.

The genomic ORF sequences of H. walsbyi DSM 16790 from NCBI RefSeq (Accession NC_008212) were retrieved and the number of UUACUCA sequences was estimated by using Perl script. For function clustering of each gene, two clusters (COGs and HaloLex Function class) were used from NCBI and HaloLex database, respectively. Clusters of Orthologous Groups of proteins (COGs) were created by comparing protein sequences encoded in complete genomes, representing major phylogenetic lineages. Each COG consists of individual proteins or groups of paralogs from at least 3 lineages and thus corresponds to an ancient conserved domain. HaloLex is a comprehensive genome information system for archaea, and the function classes of HaloLex are used to analyze all MazF-hw sensitive genes.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. An isolated polypeptide comprising an amino acid sequence that is at least 95% identical to the sequence of SEQ ID NO: 1.

2. The polypeptide of claim 1, having an mRNA interferase activity.

3. The polypeptide of claim 1, wherein the amino acid sequence is at least 99% identical to the sequence of SEQ ID NO: 1.

4. The polypeptide of claim 3, wherein the amino acid sequence comprises the sequence of SEQ ID NO: 1.

5. The polypeptide of claim 1, wherein the polypeptide has an activity of cleaving an RNA sequence having the target sequence of UUACUCA.

6. A composition comprising the polypeptide of claim 1 and a carrier.

7. A kit comprising the polypeptide of claim 1 and a buffer.

* * * * *

SEQUENCE LISTING

```
<160> NUMBER OF SEQ ID NOS: 23

<210> SEQ ID NO 1
<211> LENGTH: 123
<212> TYPE: PRT
<213> ORGANISM: Artificial Sequence
<220> FEATURE:
```

<223> OTHER INFORMATION: synthetic sequence

<400> SEQUENCE: 1

Val Thr Pro Arg Cys Arg Tyr Val Gln Val Arg Gly Asp Ile Val
1               5                   10                  15

Ile Val Asp Leu Ser Pro Thr Lys Gly Ser Glu Gln Gln Gly Thr Asn
            20                  25                  30

Arg Pro Cys Val Val Ile Gln Asn Asp Val Gly Asn Arg Asn Ser Pro
            35                  40                  45

Thr Thr Ile Ile Ala Pro Phe Thr Lys Gln Tyr Asn Pro Asp Asn Thr
        50                  55                  60

Tyr Pro Phe Glu Val Glu Val Leu Ala Ser Asn Thr Ser Leu Asn Gln
65                  70                  75                  80

Asp Ser Val Ala Asp Leu Ser Gln Ile Arg Val Asp Ile Asn Lys
                85                  90                  95

Gly Val Lys Thr Asn Ile Gly Ser Val Pro Ser Ala Arg Met Ala Lys
                100                 105                 110

Ile Asp Thr Ala Ile Lys Thr Ser Leu Gly Leu
            115                 120

<210> SEQ ID NO 2
<211> LENGTH: 375
<212> TYPE: DNA
<213> ORGANISM: Artificial Sequence
<220> FEATURE:
<223> OTHER INFORMATION: synthetic

<400> SEQUENCE: 2
catatgactc cgcgttgtcg ttacgtgcaa gtacgccgcg gcgatatcgt cattgttgac      60
ttgagtccga cgaagggtag cgagcagcag ggtaccaacc gcccttgtgt agttatccaa     120
aatgatgtgg gcaaccgtaa ctccccgacc acgatcatcg ctccgttcac gaagcagtat     180
aacccggata atacgtaccc gttcgaagta gaggtactgg catcgaatac ctcgctgaat     240
caggattcgg tggcagacct gagtcaaatc cgcgtagtgg atattaataa gggcgtgaag     300
accaatatcg gctcagttcc ttccgctcgc atggcaaaaa tcgataccgc gattaagacg     360
agtctgggtc tgtga                                                      375

<210> SEQ ID NO 3
<211> LENGTH: 13
<212> TYPE: RNA
<213> ORGANISM: Artificial Sequence
<220> FEATURE:
<223> OTHER INFORMATION: synthetic

<400> SEQUENCE: 3
aaguuacuca aag                                                         13

<210> SEQ ID NO 4
<211> LENGTH: 13
<212> TYPE: RNA
<213> ORGANISM: Artificial Sequence
<220> FEATURE:
<223> OTHER INFORMATION: synthetic

<400> SEQUENCE: 4
aaguuacucc agg                                                         13

<210> SEQ ID NO 5
<211> LENGTH: 13

-continued

```
<212> TYPE: RNA
<213> ORGANISM: Artificial Sequence
<220> FEATURE:
<223> OTHER INFORMATION: syntheic

<400> SEQUENCE: 5
aagcuacuca agg                                                        13

<210> SEQ ID NO 6
<211> LENGTH: 19
<212> TYPE: RNA
<213> ORGANISM: Artificial Sequence
<220> FEATURE:
<223> OTHER INFORMATION: synthetic

<400> SEQUENCE: 6
cauaacuuua cucaguucg                                                  19

<210> SEQ ID NO 7
<211> LENGTH: 116
<212> TYPE: PRT
<213> ORGANISM: Bacillus subtilis

<400> SEQUENCE: 7

Met Ile Val Lys Arg Gly Asp Val Tyr Phe Ala Asp Leu Ser Pro Val
1               5                   10                  15

Val Gly Ser Glu Gln Gly Gly Val Arg Pro Val Leu Val Ile Gln Asn
            20                  25                  30

Asp Ile Gly Asn Arg Phe Ser Pro Thr Ala Ile Val Ala Ala Ile Thr
        35                  40                  45

Ala Gln Ile Gln Lys Ala Lys Leu Pro Thr His Val Glu Ile Asp Ala
    50                  55                  60

Lys Arg Tyr Gly Phe Glu Arg Asp Ser Val Ile Leu Leu Glu Gln Ile
65                  70                  75                  80

Arg Thr Ile Asp Lys Gln Arg Leu Thr Asp Lys Ile Thr His Leu Asp
                85                  90                  95

Asp Glu Met Met Asp Lys Val Asp Glu Ala Leu Gln Ile Ser Leu Ala
            100                 105                 110

Leu Ile Asp Phe
        115

<210> SEQ ID NO 8
<211> LENGTH: 117
<212> TYPE: PRT
<213> ORGANISM: Clostridium perfringens

<400> SEQUENCE: 8

Met Ala Ser Leu Asn Val Lys Arg Gly Asp Ile Phe Tyr Ala Asp Leu
1               5                   10                  15

Ser Pro Val Val Gly Ser Glu Gln Gly Gly Ile Arg Pro Val Ile Ile
            20                  25                  30

Ile Gln Asn Asp Ile Gly Asn Arg Tyr Ser Pro Thr Val Ile Val Ala
        35                  40                  45

Ala Ile Thr Ser Gln Ile Asn Lys Ala Lys Leu Pro Thr His Val Glu
    50                  55                  60

Ile Ser Ser Glu Glu Tyr Gly Leu Asn Arg Asp Ser Val Val Leu Leu
65                  70                  75                  80

Glu Gln Ile Arg Thr Leu Asp Lys Lys Arg Leu Lys Glu Lys Ile Gly
                85                  90                  95
```

His Met Thr Glu Asp Asp Met Lys Lys Val Asn Lys Ser Leu Leu Ile
            100                 105                 110

Ser Leu Asn Leu Gln
        115

<210> SEQ ID NO 9
<211> LENGTH: 120
<212> TYPE: PRT
<213> ORGANISM: Staphylococcus aureus

<400> SEQUENCE: 9

Met Ile Arg Arg Gly Asp Val Tyr Leu Ala Asp Leu Ser Pro Val Gln
1               5                   10                  15

Gly Ser Glu Gln Gly Gly Val Arg Pro Val Ile Ile Gln Asn Asp
            20                  25                  30

Thr Gly Asn Lys Tyr Ser Pro Thr Val Ile Val Ala Ala Ile Thr Gly
        35                  40                  45

Arg Ile Asn Lys Ala Lys Ile Pro Thr His Val Glu Ile Glu Lys Lys
50                  55                  60

Lys Tyr Lys Leu Asp Lys Asp Ser Val Ile Leu Leu Glu Gln Ile Arg
65                  70                  75                  80

Thr Leu Asp Lys Lys Arg Leu Lys Glu Lys Leu Thr Tyr Leu Ser Asp
                85                  90                  95

Asp Lys Met Lys Glu Val Asp Asn Ala Leu Met Ile Ser Leu Gly Leu
            100                 105                 110

Asn Ala Val Ala His Gln Lys Asn
        115                 120

<210> SEQ ID NO 10
<211> LENGTH: 115
<212> TYPE: PRT
<213> ORGANISM: Nostoc commune

<400> SEQUENCE: 10

Met Ser Ile Glu Arg Gly Gln Ile Tyr Phe Val Asn Leu Asn Pro Val
1               5                   10                  15

His Gly Arg Glu Gln Ala Gly Ala Arg Pro Val Leu Val Leu Ser Thr
            20                  25                  30

Asp Ala Ile Asn Gln Leu Pro Leu Val Ile Thr Val Val Val Gly Thr
        35                  40                  45

Lys Gly Thr Asn Ile Lys Arg Asp Tyr Pro Thr Asn Ile Arg Val Ser
50                  55                  60

Pro Ser Asp Ser Gly Leu Val Ile Glu Thr Val Phe Leu Cys Phe Gln
65                  70                  75                  80

Ile Arg Ser Leu Asp Pro Asn Arg Phe Pro Thr Asp Pro Ser Gly Lys
                85                  90                  95

Leu Ser Ala Ser Lys Met Leu Glu Val Glu Thr Ala Val Arg Tyr Cys
            100                 105                 110

Leu Gly Leu
        115

<210> SEQ ID NO 11
<211> LENGTH: 146
<212> TYPE: PRT
<213> ORGANISM: Nostoc commune

<400> SEQUENCE: 11

Met Lys Pro Pro Tyr Phe Pro Asn Arg Gly Asp Ile Val Lys Leu Glu

```
              1               5                  10                 15
            Phe Gly Ser Ala Gln Gln Phe Thr Ala Glu Ser Ile Gln Arg Val Phe
                            20                 25                 30

Thr Leu Arg Asn Ser Gly Met Ser Phe Asp Asp Ile Ala Ile Thr Leu
                            35                 40                 45

Asn Asn Glu Leu Gln Gln Gly Arg Glu Gln Thr Gly Tyr Arg Pro
             50                 55                 60

Val Leu Val Ile Ser Pro Ile Lys Tyr Asn Gln Met Ala Ser Leu Val
             65                 70                 75                 80

Leu Ala Cys Pro Ile Thr Thr Asn Ala Lys Gly Leu Arg Phe Glu Val
                            85                 90                 95

Pro Leu Ile Glu Gly Met Lys Thr Lys Gly Val Val Leu Ala Asp Gln
                            100                105                110

Ile Lys Thr Leu Asp Trp Lys Ala Arg Lys Val Lys Phe Val Glu Ser
                            115                120                125

Val Thr Glu Asp Leu Ile Glu Glu Val Gln Ala Lys Leu Glu Thr Leu
                            130                135                140

Ile Leu
            145

<210> SEQ ID NO 12
            <211> LENGTH: 120
            <212> TYPE: PRT
            <213> ORGANISM: Synechocystis PCC6803

<400> SEQUENCE: 12

Met Val Met Thr Ser Thr Val Pro Gln Tyr Pro Glu Arg Gly Ala Val
             1               5                  10                 15

Ile Arg Leu Asn Leu Asn Pro Thr Gln Gly Arg Glu Gln Met Gly Glu
                            20                 25                 30

Ala Arg Pro Cys Leu Val Leu Ser His Thr Ala Phe Asn Lys Ala Arg
                            35                 40                 45

Asn Gly Leu Ile Ile Val Ser Pro Ile Thr Asn Thr Ile Lys Pro Glu
             50                 55                 60

Ile Gln Thr Leu Val Val Leu Pro Asp Gly Tyr Arg Val Gln Gly Ser
             65                 70                 75                 80

Val Ile Ala Glu Gln Ile Arg Thr Val Asp Leu Ser Leu Arg Trp Trp
                            85                 90                 95

Arg Asp Thr Gly Glu Val Leu Pro Pro Ser Phe Val Asp Gln Val Leu
                            100                105                110

Ala Val Leu Gln Leu Ile Ile Gly
                            115                120

<210> SEQ ID NO 13
            <211> LENGTH: 109
            <212> TYPE: PRT
            <213> ORGANISM: Mycobacterium tuberculosis

<400> SEQUENCE: 13

Met Thr Ala Leu Pro Ala Arg Gly Glu Val Trp Trp Cys Glu Met Ala
             1               5                  10                 15

Glu Ile Gly Arg Arg Pro Val Val Leu Ser Arg Asp Ala Ala Ile
                            20                 25                 30

Pro Arg Leu Arg Arg Ala Leu Val Ala Pro Cys Thr Thr Thr Ile Arg
                            35                 40                 45

Gly Leu Ala Ser Glu Val Val Leu Glu Pro Gly Ser Asp Pro Ile Pro
```

```
                50                  55                  60
Arg Arg Ser Ala Val Asn Leu Asp Ser Val Glu Ser Val Ser Val Ala
 65                  70                  75                  80

Val Leu Val Asn Arg Leu Gly Arg Leu Ala Asp Ile Arg Met Arg Ala
                 85                  90                  95

Ile Cys Thr Ala Leu Glu Val Ala Val Asp Cys Ser Arg
            100                 105

<210> SEQ ID NO 14
<211> LENGTH: 102
<212> TYPE: PRT
<213> ORGANISM: Mycobacterium tuberculosis

<400> SEQUENCE: 14

Met Arg Arg Gly Glu Leu Trp Phe Ala Ala Thr Pro Gly Gly Asp Arg
  1               5                  10                  15

Pro Val Leu Val Leu Thr Arg Asp Pro Val Ala Asp Arg Ile Gly Ala
                 20                  25                  30

Val Val Val Val Ala Leu Thr Arg Thr Arg Arg Gly Leu Val Ser Glu
             35                  40                  45

Leu Glu Leu Thr Ala Val Glu Asn Arg Val Pro Ser Asp Cys Val Val
         50                  55                  60

Asn Phe Asp Asn Ile His Thr Leu Pro Arg Thr Ala Phe Arg Arg Arg
 65                  70                  75                  80

Ile Thr Arg Leu Ser Pro Ala Arg Leu His Glu Ala Cys Gln Thr Leu
                 85                  90                  95

Arg Ala Ser Thr Gly Cys
            100

<210> SEQ ID NO 15
<211> LENGTH: 105
<212> TYPE: PRT
<213> ORGANISM: Mycobacterium tuberculosis

<400> SEQUENCE: 15

Met Asn Ala Pro Leu Arg Gly Gln Val Tyr Arg Cys Asp Leu Gly Tyr
  1               5                  10                  15

Gly Ala Lys Pro Trp Leu Ile Val Ser Asn Asn Ala Arg Asn Arg His
                 20                  25                  30

Thr Ala Asp Val Val Ala Val Arg Leu Thr Thr Thr Arg Arg Thr Ile
             35                  40                  45

Pro Thr Trp Val Ala Met Gly Pro Ser Asp Pro Leu Thr Gly Tyr Val
         50                  55                  60

Asn Ala Asp Asn Ile Glu Thr Leu Gly Lys Asp Glu Leu Gly Asp Tyr
 65                  70                  75                  80

Leu Gly Glu Val Thr Pro Ala Thr Met Asn Lys Ile Asn Thr Ala Leu
                 85                  90                  95

Ala Thr Ala Leu Gly Leu Pro Trp Pro
            100                 105

<210> SEQ ID NO 16
<211> LENGTH: 103
<212> TYPE: PRT
<213> ORGANISM: Mycobacterium tuberculosis

<400> SEQUENCE: 16

Met Arg Pro Ile His Ile Ala Gln Leu Asp Lys Ala Arg Pro Val Leu
  1               5                  10                  15
```

```
Ile Leu Thr Arg Glu Val Val Arg Pro His Leu Thr Asn Val Thr Val
            20                  25                  30

Ala Pro Ile Thr Thr Val Arg Gly Leu Ala Thr Glu Val Pro Val
        35                  40                  45

Asp Ala Val Asn Gly Leu Asn Gln Pro Ser Val Val Ser Cys Asp Asn
 50                  55                  60

Thr Gln Thr Ile Pro Val Cys Asp Leu Gly Arg Gln Ile Gly Tyr Leu
 65                  70                  75                  80

Leu Ala Ser Gln Glu Pro Ala Leu Ala Glu Ala Ile Gly Asn Ala Phe
                85                  90                  95

Asp Leu Asp Trp Val Val Ala
            100
```

<210> SEQ ID NO 17
<211> LENGTH: 114
<212> TYPE: PRT
<213> ORGANISM: Mycobacterium tuberculosis

<400> SEQUENCE: 17

```
Met Val Ile Ser Arg Ala Glu Ile Tyr Trp Ala Asp Leu Gly Pro Pro
 1               5                  10                  15

Ser Gly Ser Gln Pro Ala Lys Arg Arg Pro Val Leu Val Ile Gln Ser
            20                  25                  30

Asp Pro Tyr Asn Ala Ser Arg Leu Ala Thr Val Ile Ala Ala Val Ile
        35                  40                  45

Thr Ser Asn Thr Ala Leu Ala Ala Met Pro Gly Asn Val Phe Leu Pro
 50                  55                  60

Ala Thr Thr Thr Arg Leu Pro Arg Asp Ser Val Val Asn Val Thr Ala
 65                  70                  75                  80

Ile Val Thr Leu Asn Lys Thr Asp Leu Thr Asp Arg Val Gly Glu Val
                85                  90                  95

Pro Ala Ser Leu Met His Glu Val Asp Arg Gly Leu Arg Arg Val Leu
            100                 105                 110

Asp Leu
```

<210> SEQ ID NO 18
<211> LENGTH: 118
<212> TYPE: PRT
<213> ORGANISM: Mycobacterium tuberculosis

<400> SEQUENCE: 18

```
Met Met Arg Arg Gly Glu Ile Trp Gln Val Asp Leu Asp Pro Ala Arg
 1               5                  10                  15

Gly Ser Glu Ala Asn Asn Gln Arg Pro Ala Val Val Ser Asn Asp
            20                  25                  30

Arg Ala Asn Ala Thr Ala Thr Arg Leu Gly Arg Gly Val Ile Thr Val
        35                  40                  45

Val Pro Val Thr Ser Asn Ile Ala Lys Val Tyr Pro Phe Gln Val Leu
 50                  55                  60

Leu Ser Ala Thr Thr Thr Gly Leu Gln Val Asp Cys Lys Ala Gln Ala
 65                  70                  75                  80

Glu Gln Ile Arg Ser Ile Ala Thr Glu Arg Leu Leu Arg Pro Ile Gly
                85                  90                  95

Arg Val Ser Ala Ala Glu Leu Ala Gln Leu Asp Glu Ala Leu Lys Leu
            100                 105                 110
```

His Leu Asp Leu Trp Ser
        115

<210> SEQ ID NO 19
<211> LENGTH: 115
<212> TYPE: PRT
<213> ORGANISM: Mycobacterium tuberculosis

<400> SEQUENCE: 19

Met Lys Arg Leu Lys Phe Ala Arg Gly Asp Ile Val Arg Val Asn Leu
1               5                   10                  15

Asp Pro Thr Val Gly Arg Glu Gln Gln Gly Ser Gly Arg Pro Ala Leu
            20                  25                  30

Val Leu Thr Pro Ala Ala Phe Asn Ala Ser Gly Leu Ala Val Ile Ile
        35                  40                  45

Pro Ile Thr Gln Gly Gly Asp Phe Ala Arg His Ala Gly Phe Ala Val
    50                  55                  60

Thr Leu Ser Gly Ala Gly Thr Gln Thr Gln Gly Val Met Leu Cys Asn
65                  70                  75                  80

Gln Val Arg Thr Val Asp Leu Glu Ala Arg Phe Ala Lys Arg Ile Glu
                85                  90                  95

Ser Val Pro Glu Thr Ile Met Asn Glu Val Leu Gly Arg Leu Ser Thr
            100                 105                 110

Ile Leu Thr
        115

<210> SEQ ID NO 20
<211> LENGTH: 110
<212> TYPE: PRT
<213> ORGANISM: Escherichia coli

<400> SEQUENCE: 20

Met Glu Arg Gly Glu Ile Trp Leu Val Ser Leu Asp Pro Thr Ala Gly
1               5                   10                  15

His Glu Gln Gln Gly Thr Arg Pro Val Leu Ile Val Thr Pro Ala Ala
            20                  25                  30

Phe Asn Arg Val Thr Arg Leu Pro Val Val Val Pro Val Thr Ser Gly
        35                  40                  45

Gly Asn Phe Ala Arg Thr Ala Gly Phe Ala Val Ser Leu Asp Gly Val
    50                  55                  60

Gly Ile Arg Thr Thr Gly Val Val Arg Cys Asp Gln Pro Arg Thr Ile
65                  70                  75                  80

Asp Met Lys Ala Arg Gly Gly Lys Gly Leu Glu Arg Val Ala Asp Glu
                85                  90                  95

Val Val Glu Glu Ala Leu Leu Arg Leu Gln Ala Val Val Glu
            100                 105                 110

<210> SEQ ID NO 21
<211> LENGTH: 116
<212> TYPE: PRT
<213> ORGANISM: Escherichia coli

<400> SEQUENCE: 21

Met Val Lys Lys Ser Glu Phe Glu Arg Gly Asp Ile Val Leu Val Gly
1               5                   10                  15

Phe Asp Pro Ala Ser Gly His Glu Gln Gln Gly Ala Gly Arg Pro Ala
            20                  25                  30

Leu Val Leu Ser Val Gln Ala Phe Asn Gln Leu Gly Met Thr Leu Val

```
                35                  40                  45
Ala Pro Ile Thr Gln Gly Gly Asn Phe Ala Arg Tyr Ala Gly Phe Ser
 50                  55                  60
Val Pro Leu His Cys Glu Gly Asp Val His Gly Val Val Leu Val
 65                  70                  75                  80
Asn Gln Val Arg Met Met Asp Leu His Ala Arg Leu Ala Lys Arg Ile
                 85                  90                  95
Gly Leu Ala Pro Glu Ala Val Ile Leu Asp Ala Leu Ala Arg Val Gln
                100                 105                 110
Thr Leu Phe Asp
        115

<210> SEQ ID NO 22
<211> LENGTH: 122
<212> TYPE: PRT
<213> ORGANISM: Myxococcus xanthus

<400> SEQUENCE: 22

Met Pro Pro Glu Arg Ile Asn Arg Gly Asp Val Phe Trp Val Glu Pro
 1               5                  10                  15
Asp Asp Ser Arg Gly Pro Val Pro Ser Tyr Ser His Pro His Val Val
                20                  25                  30
Val Gln Asp Asp Val Phe Asn His Ser Arg Ile Thr Thr Val Val Val
                35                  40                  45
Cys Ala Leu Thr Ser Asn Leu His Arg Ala Ser Glu Pro Gly Asn Val
 50                  55                  60
Leu Leu Glu Val Gly Glu Gly Asn Leu Pro Lys Gln Ser Val Val Val
 65                  70                  75                  80
Val Ser Gln Val Ser Ser Val Asp Lys Ala Arg Leu Gly Glu Arg Ile
                85                   90                  95
Gly Ala Leu Ser Asp Ala Arg Val Glu Gln Ile Leu Ala Gly Leu Arg
                100                 105                 110
Phe Gln Gln Val Ser Phe Phe Ala Arg Pro
                115                 120

<210> SEQ ID NO 23
<211> LENGTH: 111
<212> TYPE: PRT
<213> ORGANISM: Escherichia coli

<400> SEQUENCE: 23

Met Val Ser Arg Tyr Val Pro Asp Met Gly Leu Ile Trp Val Asp
 1               5                  10                  15
Phe Asp Pro Thr Lys Gly Ser Glu Gln Ala Gly His Arg Pro Ala Val
                20                  25                  30
Val Leu Ser Pro Phe Met Tyr Asn Asn Lys Thr Gly Met Cys Leu Cys
                35                  40                  45
Val Pro Cys Thr Thr Gln Ser Lys Gly Tyr Pro Phe Glu Val Val Leu
 50                  55                  60
Ser Gly Gln Glu Arg Asp Gly Val Ala Leu Ala Asp Gln Val Lys Ser
 65                  70                  75                  80
Ile Ala Trp Arg Ala Arg Gly Ala Thr Lys Lys Gly Thr Val Ala Pro
                 85                  90                  95
Glu Glu Leu Gln Leu Ile Lys Ala Lys Ile Asn Val Leu Ile Gly
                100                 105                 110
```